United States Patent
Pisupati et al.

(10) Patent No.: US 7,233,867 B2
(45) Date of Patent: Jun. 19, 2007

(54) EDDY CURRENT INSPECTION METHOD AND SYSTEM

(75) Inventors: Preeti Pisupati, Karnataka (IN); Gigi Olive Gambrell, West Chester, OH (US); Shyamsunder Tondanur Mandayam, Karnataka (IN); Amitabha Dutta, Fort Worth, TX (US)

(73) Assignee: General Electric Company, Niskayuna, NY (US)

( * ) Notice: Subject to any disclaimer, the term of this patent is extended or adjusted under 35 U.S.C. 154(b) by 96 days.

(21) Appl. No.: 11/100,302

(22) Filed: Apr. 6, 2005

(65) Prior Publication Data

US 2006/0229833 A1 Oct. 12, 2006

(51) Int. Cl.
*G06F 19/00* (2006.01)

(52) U.S. Cl. .......... 702/64; 324/255; 382/152

(58) Field of Classification Search .......... 702/35, 702/38, 64; 324/232, 240, 242, 255; 378/58; 381/152; 356/237.5
See application file for complete search history.

(56) References Cited

U.S. PATENT DOCUMENTS

| 5,345,514 | A | 9/1994 | Mahdavieh et al. ........ 282/152 |
| 5,371,462 | A | 12/1994 | Hedengren et al. ......... 324/255 |
| 5,442,286 | A | 8/1995 | Sutton, Jr. et al. .......... 324/242 |
| 6,157,699 | A | 12/2000 | Dunn .......................... 378/58 |
| 6,378,871 | B1 | 4/2002 | Roberts ....................... 273/444 |
| 6,630,996 | B2 * | 10/2003 | Rao et al. ................. 356/237.5 |

FOREIGN PATENT DOCUMENTS

EP 0437280 7/1991

OTHER PUBLICATIONS

M. Sezgin et al., "Survey over image thresholding techniques and quantitative performance evaluation," Journal of Electronic Imaging, vol. 13, No. 1, Jan. 2004, pp. 146-168.
M. Sezgin et al., "Selection of thresholding method for non-destructive testing applications," IEEE, Proceedings 2001 International Conference on Image Processing, vol. 1 of 3. Conf. 8, Oct. 7, 2001, pp. 764-767.
N. Nacereddine et al., "Non-Parametric histogram-Based Thresholding Methods for Weld Defect Detection in Radiography," Transactions on Engineering, Computing & Technology, ISSN 1305-5313, vol. 9, Nov. 2005, pp. 213-217.

(Continued)

*Primary Examiner*—Bryan Bui
*Assistant Examiner*—John Le
(74) *Attorney, Agent, or Firm*—Penny A. Clarke; Patrick K. Patnode

(57) ABSTRACT

An eddy current inspection system and method for inspecting a component is provided. The system includes an eddy current probe for sensing eddy currents from the component and an analog to digital converter configured for converting eddy currents to digital signals. The system also includes a processor configured for generating an eddy current image from the digital signals and pre-processing the image to enhance a quality of the image. The processor is configured to identify regions displaying flaw patterns and calculating a defect characterizing parameter for the identified regions.

25 Claims, 5 Drawing Sheets

OTHER PUBLICATIONS

J. Moysan et al., "Adapting an ultrasonic image threshold method to eddy current images and defining a validation domain of the thresholding method," NDT&E International, vol. 32, No. 2, Mar. 1999, pp. 79-84.

B. Raj et al., "Frontiers in NDE research nearing maturity for exploitation to ensure structural integrity of pressure retaining components," International Journal of Pressure Vessels and Piping, Elsevier Science Publishers, vol. 83, No. 5, May 2006, pp. 322-335.

EP Search Report, EP06251930, Jul. 5, 2006.

* cited by examiner

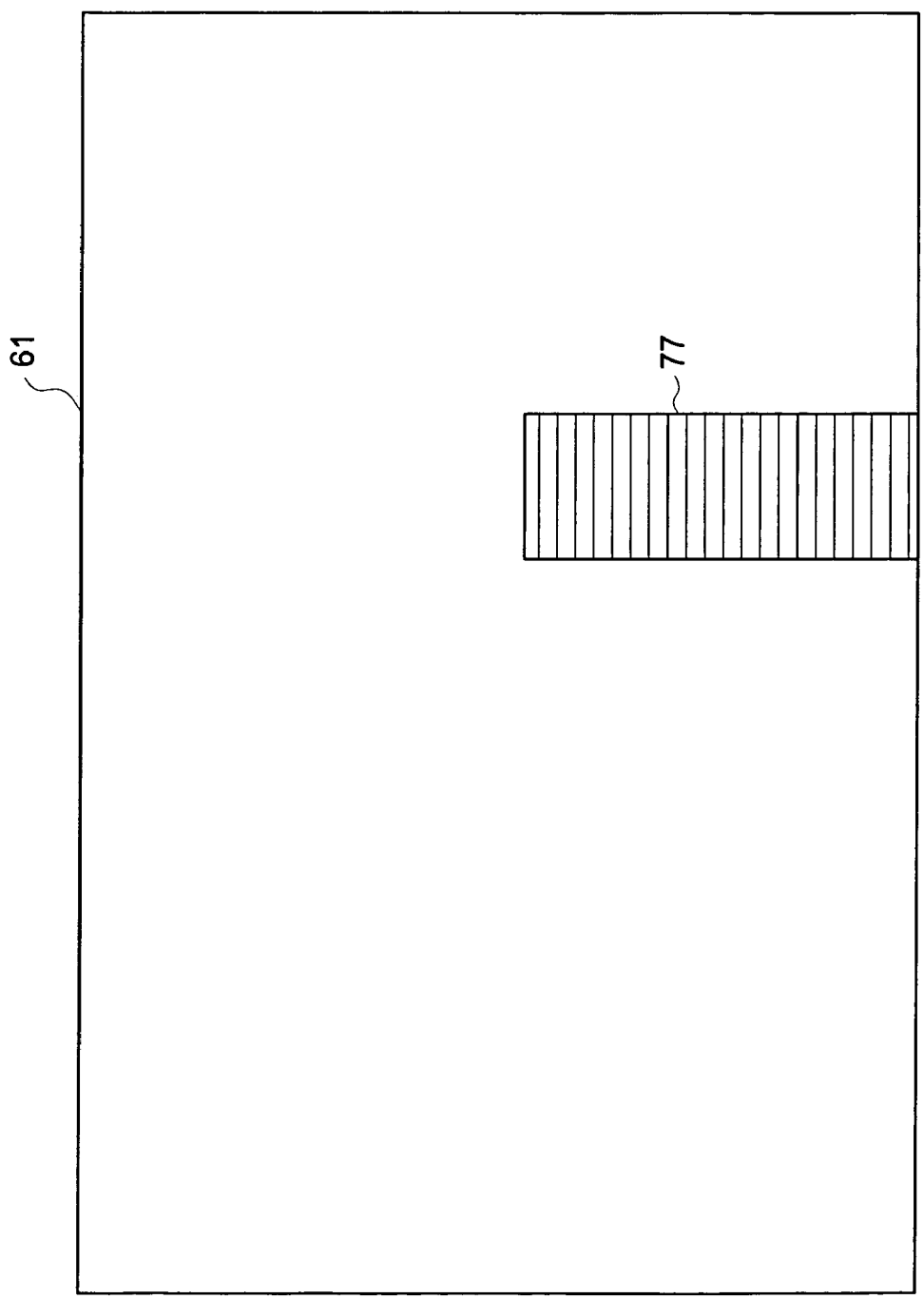

EDDY CURRENT INSPECTION METHOD AND SYSTEM

BACKGROUND

The invention relates generally to inspection systems and more specifically to a method and system for automated eddy current nondestructive testing.

Eddy current inspection is a commonly used technique for nondestructive inspection of aircraft engine and other industrial components for surface flaws. The technique is based on the principle of electromagnetic induction, wherein a drive coil carrying alternating currents induces eddy currents into a part under test. In the case of a flaw in the test specimen, as for example, a crack or a discontinuity, the eddy current flow within the test specimen alters, which can be detected by one or more sense coils. The detected signals are used to generate an eddy current image, which can be analyzed further to detect the presence of flaws in image.

Attempts have been made to develop automatic flaw detection processes for eddy current images. U.S. Pat. No. 5,345,514, Mahdavieh et al., entitled "Method for inspecting components having complex geometric shapes," discloses one such technique, which uses references images from adjacent structurally similar portions to perform the processing. Typically, a surface of a component is scanned with an eddy current probe and a two-dimensional image of the scanned portion is generated using the eddy current signals received during scanning. The image is preprocessed to reduce any signals relative to the background pixel intensities in the image caused by geometric characteristics and background noise common to all similarly shaped structural portions. Any suspected defect regions are identified from the preprocessed image, and a defect characterizing parameter is determined for each suspected defect region. Typically, if any defect characterizing parameter exceeds a predetermined reference value, the suspected defect region is rejected.

The above described method may have certain disadvantages, including a lower probability of detection, due to less effective encapsulation of the flaw patterns seen in the eddy current images acquired by the system. Another disadvantage of the above described process, is the fact that two reference images obtained from adjacent structural portions of the component under inspection are required as inputs to the process, for suppressing strong edge signals which mask the underlying crack signals. Availability of such reference images may be difficult for real-time inspections.

Thus, there is a need to develop a more precise method of eddy current inspection that would automatically detect defects in real time and characterize the size of the defect.

BRIEF DESCRIPTION

Briefly, according to one embodiment of the invention, a method for performing automatic flaw detection and characterization for a component is provided. The method includes receiving an image of the component. The image is generated by an eddy current inspection system and the image includes a number of pixels. The method further includes pre-processing the image to enhance a quality of the image and processing the image to identify regions displaying flaw patterns and calculating a defect characterizing parameter for the identified regions. The defect characterizing parameter is a function of an energy of the identified region, an entropy of the identified region or any combination thereof.

In another embodiment, an eddy current inspection system for inspecting a component is provided. The system includes an eddy current probe for sensing eddy currents induced in the component and for generating sensing signals and an analog to digital converter configured for converting the sensing signals to digital signals. The system further includes a processor configured for generating an eddy current image from the digital signals and pre-processing the image to enhance a quality of the image. The processor is further adapted to identify regions displaying flaw patterns by calculating a defect characterizing parameter for the identified regions. The defect characterizing parameter is calculated based on an energy of the identified region, an entropy of the identified region or any combination thereof.

DRAWINGS

These and other features, aspects, and advantages of the present invention will become better understood when the following detailed description is read with reference to the accompanying drawings in which like characters represent like parts throughout the drawings, wherein:

FIG. 6 illustrates another image with labeled true flaw regions and labeled false flaw regions.

DETAILED DESCRIPTION

Figure 1:
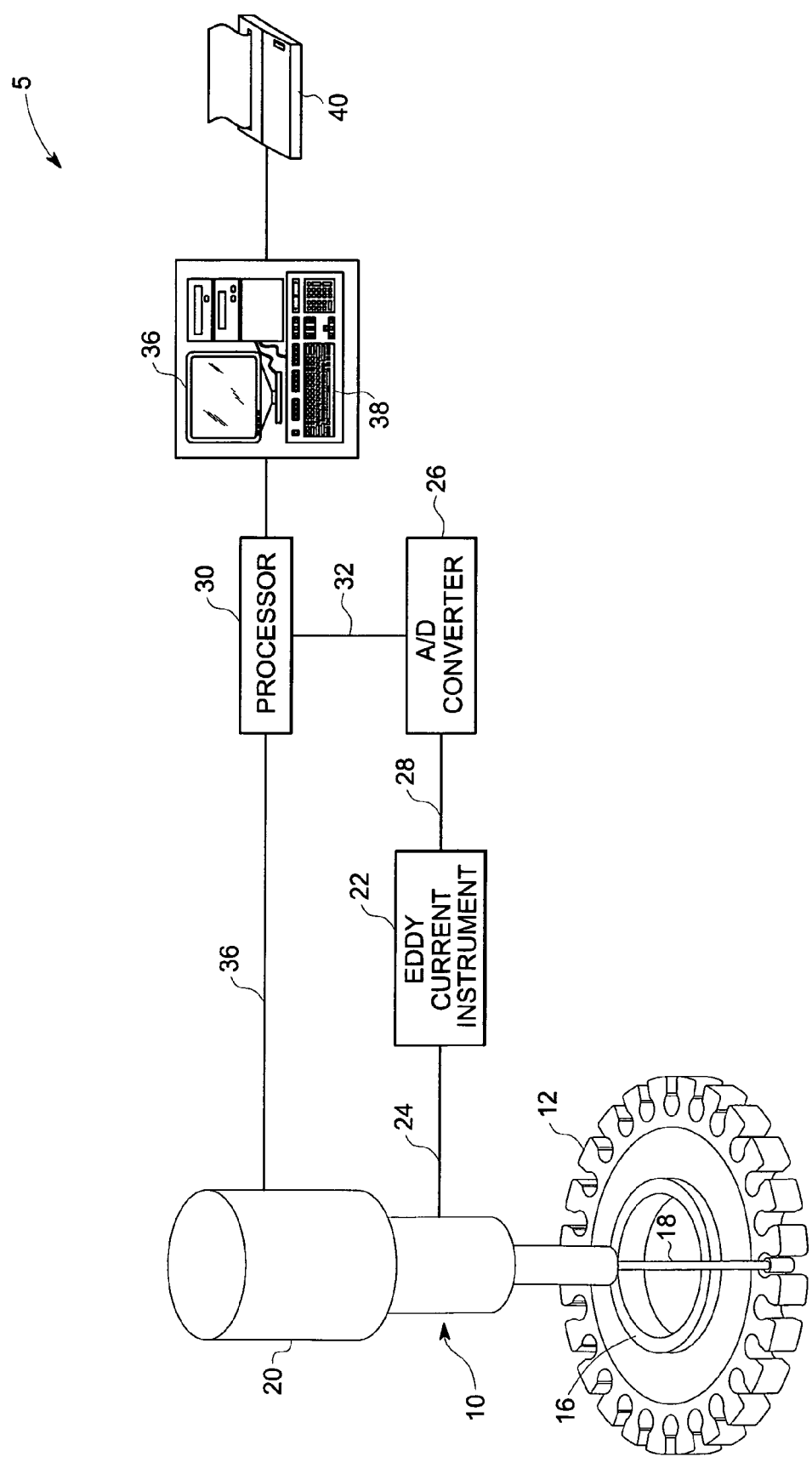
FIG. 1 is a schematic diagram of an exemplary automated eddy current flaw detection system.

FIG. 1 is a block diagram of one embodiment of an automated eddy current flaw detection system 5. The system includes an automated eddy current surface flaw detection apparatus 10 for inspecting a component 12. Examples of the component include turbine blades, the gear teeth of a gear, dovetail slots of a gas turbine engine disk. For purposes of convenience, FIG. 1 is described with respect to inspecting the dovetail slots 14 of a gas turbine engine disk 12; although, those skilled in the art will recognize that the invention is equally applicable to other components.

As used herein, "adapted to", "configured" and the like refer to devices in a system to allow the elements of the system to cooperate to provide a described effect; these terms also refer to operation capabilities of electrical or optical elements such as analog or digital computers or application specific devices (such as an application specific integrated circuit (ASIC)), amplifiers or the like that are programmed to provide an output in response to given input signals, and to mechanical devices for optically or electrically coupling components together.

For the exemplary embodiment of FIG. 1, the turbine disk 12 is mounted on a fixture 16 of eddy current apparatus 10 to hold disk 12 in place during inspection. Apparatus 10 further includes an eddy current coil/probe 18. Eddy current probe 18 is mounted to a probe manipulator 20 which moves probe 18 within dovetail slot 14 to substantially completely scan the interior of slot 14 during inspection.

For the exemplary embodiment of FIG. 1, eddy current probe 18 is electrically connected to an eddy current instrument 22 by a data link 24. Eddy current instrument 22 generates electrical signals responsive to the eddy currents induced within the surface of dovetail slot 14 during scanning of the slot by probe 18.

The electrical signals generated by eddy current instrument 22 are received by an analog to digital (A/D) converter 26 over data communications link 28. A/D converter 26 is configured to convert the analog eddy current signals to digital signals which can be stored and processed by a processor 30 to generate a two-dimensional eddy current image of dovetail slot 14.

The digital signals are transmitted from A/D converter 26 to processor 30 by a communications link 32. The eddy current images may be displayed on a video monitor 34. Processor 30 is also interconnected to probe manipulator 20 by a communications link 36 to control the scanning of the dovetail slots 14. A keyboard 38 is provided to facilitate operator control of the inspection of disk 12 and a printer 40 may be provided to generate hard copies of the images.

Figure 2:
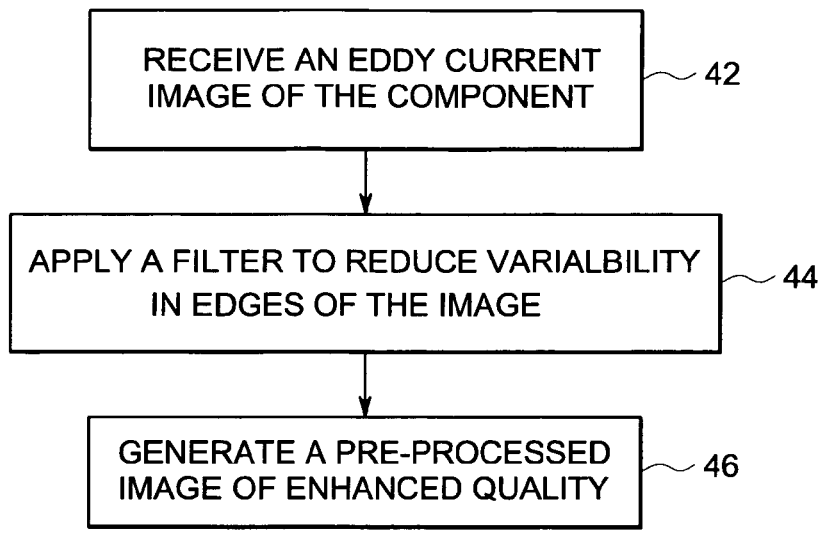
FIG. 2 is a flow chart illustrating the details of a pre-processing step performed by the eddy current flaw detection system.

Processor 30 is configured to detect and characterize flaws in the component. The method by which the processor 30 is configured to detect and characterize flaws includes preprocessing steps and processing steps. The pre-processing steps are described in greater detail with reference to the flow chart illustrated in FIG. 2. Each step is described in further detail below.

The pre-processing steps are performed to enhance a quality of the eddy current image received from the analog to digital converter as shown in step 42. In step 44, a filter is applied to the eddy current image to reduce variability in edges of the image. The filtering techniques used are based on averaging out the values in the given image. By applying the filter, the edge effects are smoothened in the eddy current image, which can be easily removed in the subsequent steps. In one embodiment, a 7 by 7 pixel moving average filter is employed. Thus, it is seen that the pre-processing step does not require reference images. In step 46, a pre-processed image of enhanced quality is generated.

Figure 3:
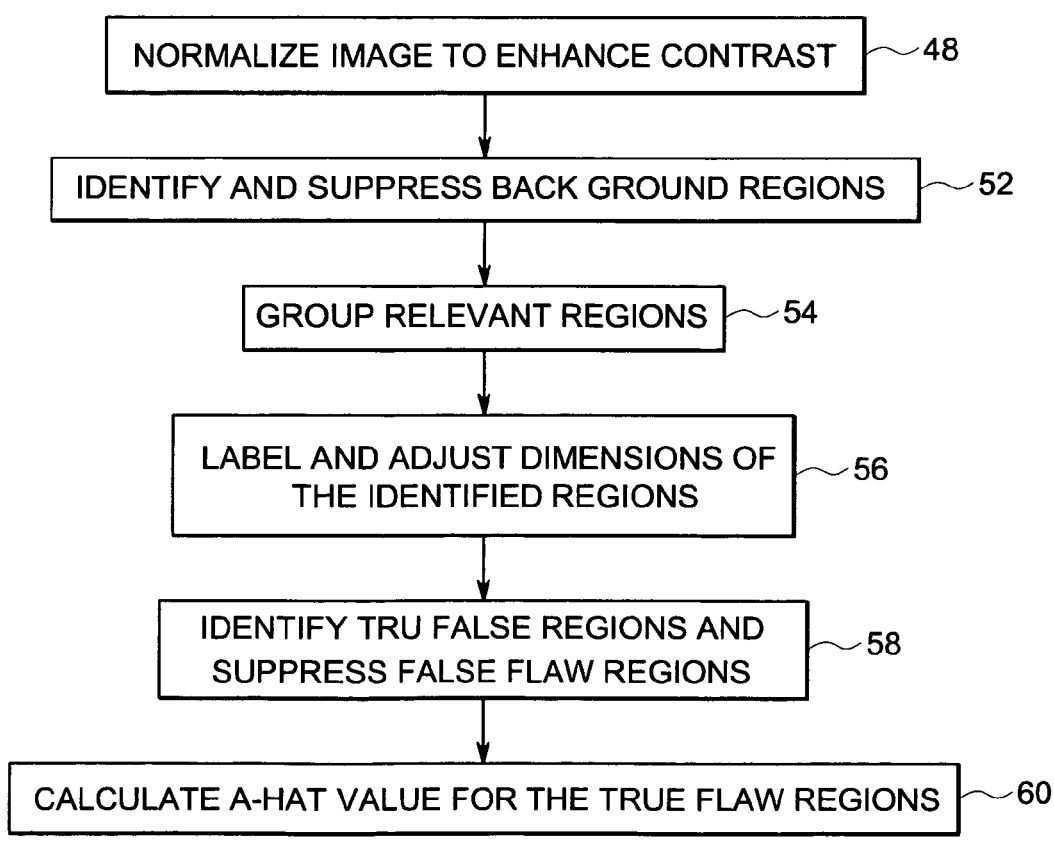
FIG. 3 is a flow chart illustrating exemplary details of a processing step performed by the eddy current flaw detection system.

The pre-processed image is further processed to identify regions in the image that display distinctive patterns. These may or may not include flaw patterns. These regions will be referred to as identified regions. The processing steps are described in greater detail with reference to the flow chart illustrated in FIG. 3. Each step is described in further detail below.

In step 48, the image is normalized to enhance contrast of the image. In one embodiment, normalization is performed by computing a median of the pixels in the image. The median value is then subtracted from each pixel of the image. The resulting normalized image enhances contrast thus making it easier to detect flaws in the subsequent steps. By applying the filter, the edge effects are substantially removed from the image.

In step 52, background regions in the image are identified and suppressed. Background regions correspond to regions in the image that are substantially free of flaws. In one embodiment, background regions are identified by calculating a mean and standard deviation of the median of the image. Bandpass filters, notch filters, signal to noise ration (SNR), area proximity and adaptive thresholds are also used to eliminate background noise.

Figure 4:
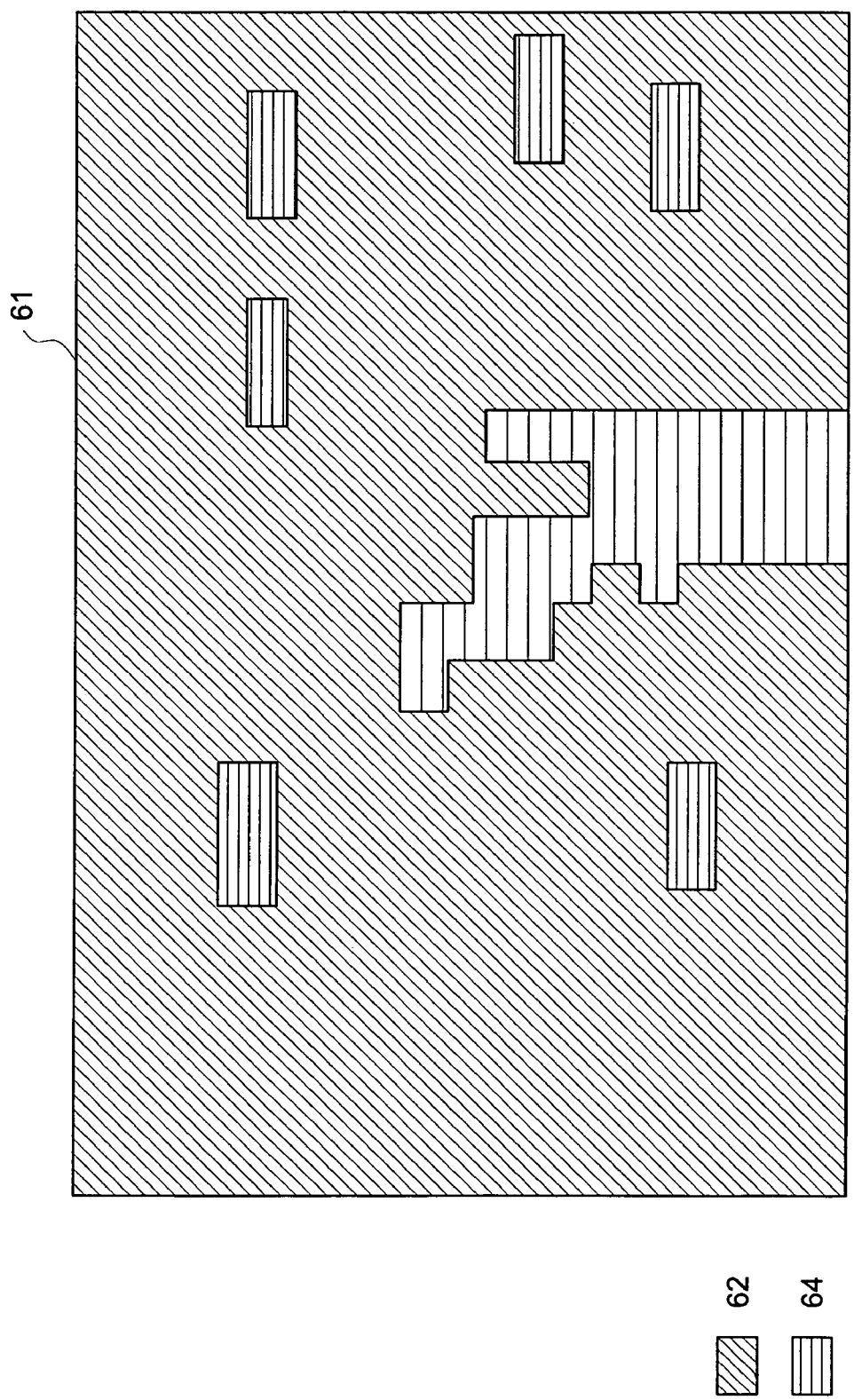
FIG. 4 illustrates an exemplary image with background regions and regions identified as containing flaws.

FIG. 4 illustrates a binary image 61 which is a result of step 52. This image 61 includes background regions 62 and identified regions 64. Identified regions are the regions that were identified in the pre-processing steps. In the illustrated embodiment, the background region is represented by a gray scale value of zero and the identified regions are represented by a gray scale value of one.

In step 54, two or more identified regions referred as 64 are grouped as one identified region based on few criteria by a technique called gap filling. In one embodiment, if a distance between two or more identified regions is less than a threshold value, gap filling is performed. Gap filling is technique by which the gray scale value of background region 62 between two identified regions 64 is changed from zero to one.

Figure 5:
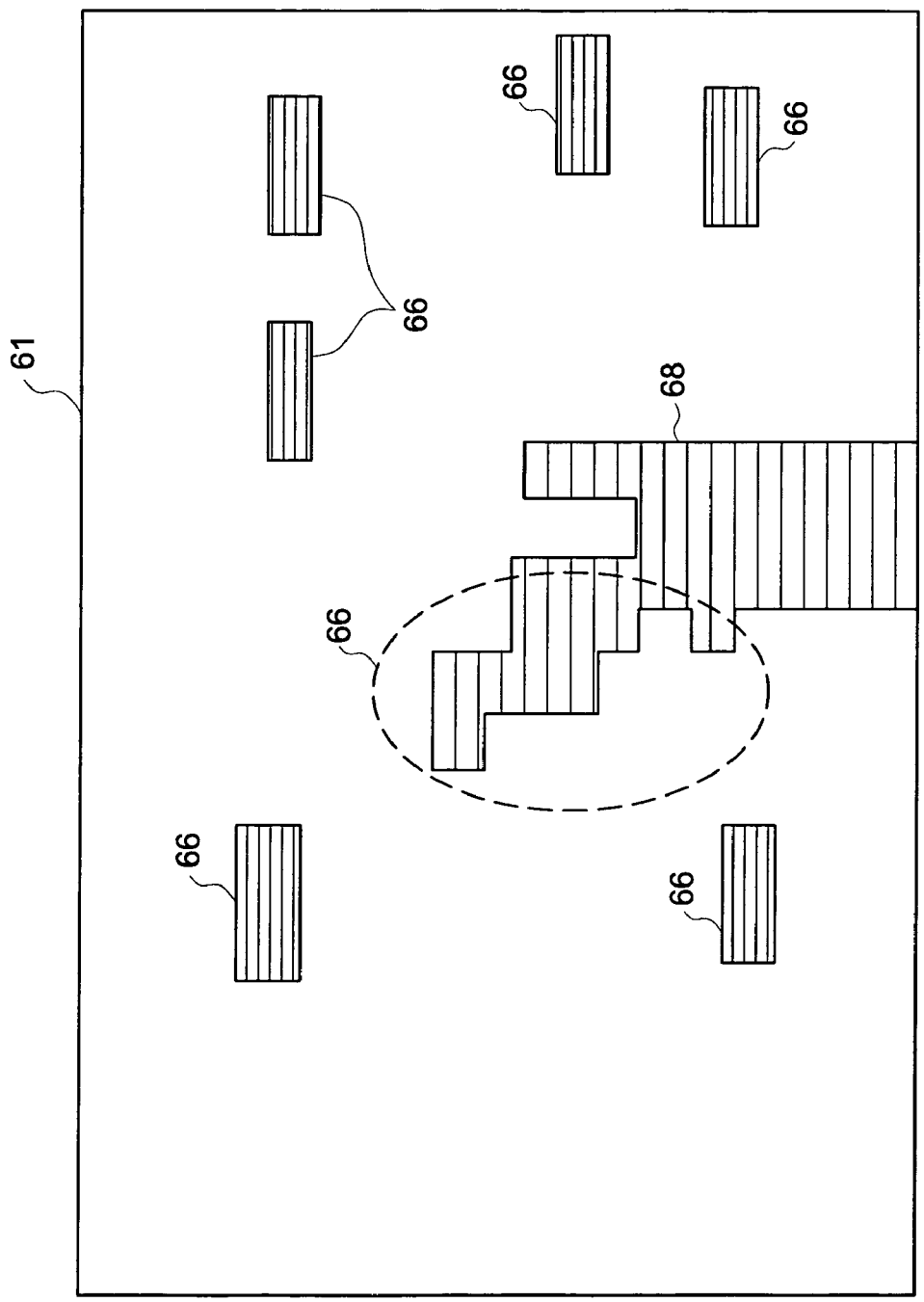
FIG. 5 illustrates another exemplary image with true flaw regions and false flaw regions.

In step 56, the identified regions are labeled and dimensions of the identified regions are adjusted. The identified regions include true flaw regions and false flaw regions, the true flaw region being the region that displays the flaw pattern. The dimensions of the identified regions are approximated to a closed shape. In one embodiment, the closed shape is a rectangle. Labeling and adjusting the dimensions of the identified regions may be performed simultaneously. FIG. 5 depicts an exemplary image 61 that includes false flaw regions 66 and true flaw regions 68.

In step 58, the true flaw regions are identified as they display a flaw pattern that represents a unique characteristic of the flaw. In one embodiment, the flaw pattern is a Checker Board Effect. The false flaw regions are then suppressed. FIG. 6 depicts an exemplary image where the true flaw regions have been identified and the false flaw region 66 of FIG. 6 has been suppressed. For the exemplary embodiment of FIG. 6, the true flaw regions have been approximated to a rectangular shape as described in step 56. The true flaw region has been labeled as 77. In one embodiment, each true flaw region is labeled using a unique gray scale value.

In step 60, features of the true flaw regions are extracted by calculating a defect characterizing parameter. The features can be either one-dimensional or two-dimensional, based on the signal characteristics and the dimensions of the closed shape. In one embodiment, the dimensions of the closed shape are used to suppress false flaw regions. The A-hat value which uses the above features can be used to characterize the flaw. In one embodiment, the defect characterizing parameter is represented by the features like energy, entropy. The A-hat value is calculated based on an energy of the identified region, an entropy of the identified region or any combination thereof.

According to an exemplary embodiment the A-hat value may be calculated using any one of the equations given below:

$$A\text{hat} = (\text{Energy} \times \text{Entropy})^{1/4} \quad \text{Equation (1)},$$

$$A\text{hat} = (\text{Mean Energy} \times \text{Entropy})^{1/4} \quad \text{Equation (2), and}$$

$$A\text{hat} = e^{(\text{Energy}^{1/16} \times \text{Entropy}^{1/16})} \quad \text{Equation (3)}.$$

The above described method does not use reference images to detect and characterize the flaws. Hence, the method significantly reduces the inspection time and is more suitable for real time applications. The method can be used to detect flaws of sizes varying from about 10 mils to about 204 mils. The method also provides reduced false calls, as the false flaw patterns are identified and suppressed.

Although only certain features of the invention have been illustrated and described herein, many modifications and changes will occur to those skilled in the art. It is, therefore, to be understood that the appended claims are intended to cover all such modifications and changes as fall within the true spirit of the invention.

The invention claimed is:

1. A method for performing automatic flaw detection and characterization for a component, the method comprising:
   receiving an image of the component, wherein the image is generated by an eddy current inspection system and comprises a plurality of pixels;
   pre-processing the image to enhance at least one quality of the image; and
   processing the image to detect and characterize flaws in the component, wherein the processing comprises:
      identifying regions in the image displaying respective distinctive patterns;
      calculating a defect characterizing parameter for the region displaying the flaw pattern, wherein the defect characterizing parameter is a function of at least one of an energy of the identified region, an entropy of the identified region or any combination thereof; and
      using the defect characterizing parameter to detect a presence of a flaw in the component.

2. The method of claim 1, wherein the pre-processing step comprises applying a moving average filter to the image.

3. The method of claim 1, wherein the processing step further comprises normalizing the image.

4. The method of claim 3, wherein the normalizing comprises calculating a mean of median values falling in a specified standard deviation of the image and subtracting the mean from each pixel of the image.

5. The method of claim 4, wherein the normalizing further comprises using band pass filters, notch filters and adaptive thresholds.

6. The method of claim 1, wherein the processing step comprises identifying and suppressing a plurality of background regions in the image, wherein background regions correspond to regions in the image that are substantially free of flaws.

7. The method of claim 1, wherein the processing step further comprises gap filling.

8. The method of claim 1, wherein the processing step further comprises:
   generating a binary mask for the image, and
   labeling the identified regions and adjusting a dimension of the identified regions, wherein the identified regions comprise a plurality of true flaw regions and false flaw regions, and wherein the true flaw region displays the flaw pattern.

9. The method of claim 8, wherein the processing further comprises suppressing the false flaw regions.

10. The method of claim 8, wherein the adjusting further comprises approximating each of the flaw regions to a closed shape.

11. The method of claim 10, wherein the closed shape is a rectangle.

12. The method of claim 8, wherein the labeling and the approximating are performed simultaneously.

13. The method of claim 8, wherein the processing comprises extracting a plurality of features from the true flaw regions approximated to the closed shape.

14. The method of claim 13, wherein the features comprise the energy of the true flaw region, the entropy of the true flaw region and a dimension of the closed shape.

15. The method of claim 1, wherein the flaw pattern comprises a Checker Board Pattern.

16. The method of claim 1, wherein the defect characterizing parameter is calculated by determining an A-hat value using an equation $$A\text{hat} = (\text{Energy} \times \text{Entropy})^{1/4}.$$

17. The method of claim 1, wherein the defect characterizing parameter is calculated by determining an A-hat value using the equation $$A\text{hat} = (\text{Mean Energy} \times \text{Entropy})^{1/4}.$$

18. The method of claim 1, wherein the defect characterizing parameter is calculated by determining an A-hat value using the equation $$A\text{hat} = e^{(\text{Energy}^{1/16} \times \text{Entropy}^{1/16})}.$$

19. An eddy current inspection system for inspecting a component, the system comprising:
   an eddy current probe configured for sensing a plurality of eddy currents induced in the component and to generate a plurality of sensing signals;
   an analog to digital converter configured for converting the sensing signals to a respective plurality of digital signals;
   a processor configured for:
   generating an image from the digital signals;
   pre-processing the image to enhance a quality of the image;
   identifying a plurality of regions in the image displaying a respective plurality of flaw patterns by calculating a defect characterizing parameter for the identified regions, wherein the defect characterizing parameter is calculated based on at least one of an energy of the identified region, an entropy of the identified region or any combination thereof; and
   using the defect characterizing parameter to detect a presence of a flaw in the component.

20. The system of claim 19, wherein the processor is further configured for performing at least one of:
   pre-processing the image by applying a moving average filter; and
   pre-processing the image by normalizing the image.

21. The system of claim 19, wherein the processor is further configured to generate a binary mask of the image and to identify and suppress a plurality of background regions in the image, wherein the background regions correspond to regions in the image that are substantially free of flaws.

22. The system of claim 19, wherein the processor is further configured to perform a gap filling operation on the identified regions;
   label the identified regions and adjust a dimension of the identified regions, wherein the identified regions comprise a plurality of true flaw regions and false flaw regions, and wherein the true flaw region displays the flaw pattern; and
   suppress the false flaw regions.

23. The system of claim 22, wherein the processor is configured to adjust the dimension by approximating each of the true flaw regions to a closed shape.

24. The system of claim 23, wherein the processor is further configured to extract a plurality of features from the true flaw regions, wherein the features comprise the energy of the true flaw region, the entropy of the true flaw region and a dimension of the closed shape.

25. The system of claim 22, wherein the processor is configured to label and adjust the identified regions simultaneously.

* * * * *